United States Patent [19]
Paul et al.

[11] Patent Number: 5,876,982
[45] Date of Patent: Mar. 2, 1999

[54] **STRAIN OF *KLEBSIELLA PNEUMONIAE*, SUBSP. *PNEUMONIAE*, AND A PROCESS FOR THE PRODUCTION OF A POLYSACCHARIDE CONTAINING L-FUCOSE**

[75] Inventors: François Marie Bernard Paul, Toulouse; David Frank Perry, Beauvais; Pierre Frédéric Monsan, Blagnac, all of France

[73] Assignee: BioEurope, Anet, France

[21] Appl. No.: 875,388

[22] PCT Filed: Jan. 25, 1996

[86] PCT No.: PCT/FR96/00127

§ 371 Date: Jul. 25, 1997

§ 102(e) Date: Jul. 25, 1997

[87] PCT Pub. No.: WO96/23057

PCT Pub. Date: Aug. 1, 1996

[30] Foreign Application Priority Data

Jan. 26, 1995 [FR] France .................................. 95 00898

[51] Int. Cl.$^6$ ................ C12P 19/04; C12N 1/12
[52] U.S. Cl. ........................................ 435/101; 435/252.1
[58] Field of Search ................................. 435/101, 252.1

[56] References Cited

U.S. PATENT DOCUMENTS

| | | | |
|---|---|---|---|
| 4,298,691 | 11/1981 | Veeder et al. | 435/101 |
| 5,330,903 | 7/1994 | Kerr et al. | 435/101 |
| 5,336,619 | 8/1994 | Matsuyama et al. | 435/280 |
| 5,354,671 | 10/1994 | Pollock | 435/101 |

OTHER PUBLICATIONS

Bergey's Manual of Systematic Bacteriology 1984, vol. 1, pp. 463–465.

R. T. Engeish "Ornithie–sorbitol agar as an aid to the identification of *Kl. penumoniae* in sputum" Medical Laboratory Science (1980) 37, pp. 365–366.

*Structure of the Capsular Polysaccharide of Klebsiella K–Type 63*, Jean-Paul Joseleau and Marie-France Marais; vol. 77, pp. 183–190 (1979), Carbohydrate Res.

*Primary Examiner*—Sandra E. Saucier
*Assistant Examiner*—Vera Afremova

[57] ABSTRACT

The present invention discloses a new strain of *Klebsiella pneumoniae* subsp. *pneumoniae* BEC1000 CNCMI-1507 which produces industrially useful quantities of a polysaccharide containing L-fucose. Also disclosed is a process of producing the polysaccharide using this strain and mutants thereof. The polysaccharide has properties which are particularly useful to the cosmetics industry.

6 Claims, No Drawings

STRAIN OF *KLEBSIELLA PNEUMONIAE*, SUBSP. *PNEUMONIAE*, AND A PROCESS FOR THE PRODUCTION OF A POLYSACCHARIDE CONTAINING L-FUCOSE

This application is a 371 of PCT/FR96/00127 filed Jan. 25, 1996.

BACKGROUND OF THE INVENTION

1. Field of the Invention

The invention concerns a new strain of *Klebsiella pneumoniae*, subsp. *pneumoniae*, and a process for the production of a polysaccharide containing L-fucose using this strain.

The new strain of *Klebsiella pneumoniae* subsp. *pneumoniae* (hereinafter termed BEC 1000) of the invention was deposited in the Collection Nationale de Cultures de Microorganismes, 25, rue du Docteur Roux, 75724 PARIS CEDEX 15, France, on 16 Dec. 1994, in accordance with the provisions of the Treaty of Budapest. It was given the registration number I-1507.

2. Technological Background

The use of bacterial strains of the genus Klebsiella to produce polysaccharides containing L-fucose is known in itself.

In Carbohydrate Research, 77 (1979), pages 183–190, J. P. JOSELEAU and M. -F. MARAIS describe a capsular polysaccharide containing D-galactose, L-fucose and D-galacturonic acid in a ratio of 1:1:1 originating from a strain of Klebsiella K-63.

In U.S. Pat. No. 4,298,691, G. T. VEEDER and K. S. KANG describe a process for the production of a S-156 heteropolysaccharide by culture of a strain of *Klebsiella pneumoniae*, close to the above strain K-63, deposited in the American Type Culture Collection, on 12$^{th}$ May 1988, as N° ATCC 31646, in an aqueous nutrient medium by aerobic fermentation of a source of assimilatable glucides, such as hydrolysed starch. That heteropolysaccharide contains D-galacturonic acid, D-galactose and L-fucose in an approximate molar ratio of 23:21:26.

SUMMARY OF THE INVENTION

Following intensive research, the present inventors have discovered a new strain of *K. pneumoniae* subsp. *pneumoniae*, called BEC 1000, which has been shown to be capable of producing industrially useful quantities of a polysaccharide containing L-fucose which has properties which are of interest to the cosmetics industry, such as feel, moisturising ability, emulsion stabilisation capacity and perfume persistency power.

DETAILED DESCRIPTION OF THE PREFERRED EMBODIMENTS OF THE INVENTION

Strain BEC 1000 has been isolated from the sludge from a sewerage plant. A sample of 1 g of sludge was used to inoculate 10 ml of culture medium placed in a 100 ml conical flask. The culture medium contained, per liter, 0.02 g of yeast extract, 10 g of glucose, 9 g of $K_2HPO_4$, 3 g of $KH_2PO_4$, 1 g of $(NH_4)_2SO_4$, and 0.2 g of $MgSO_4,7H_2O$, had a pH of 7.2 and had been autoclaved at 110° C. for 30 minutes before use. The culture period was 6 days at 30° C., with stirring at 120 rpm. A series of increasing dilutions of the culture medium was prepared and each was plated onto Petri dishes containing culture medium to which 2% by weight of agar had been added. After two days, colonies with a pronounced mucoid appearance were isolated.

The strain of the invention was selected after re-culturing the strongly mucoid colonies in culture medium because it provided a particularly positive response to the following determinations:

determination of 6-deoxyhexoses (methylpentoses) using the spectrophotometric method of Z. DISCHE and L. B. SHETTLES: "A specific color reaction of methylpentoses and a spectrophotometric micromethod for their determination", J. Biol. Chem. 175, 595–603 (1948);

determination of L-fucose by thin layer chromatography (TLC);

determination of L-fucose by high-pressure liquid chromatography (HPLC);

The BEC 1000 strain of the invention has the following characteristics:

CELLULAR APPEARANCE—homogeneous bacillae, with no noticeable arrangement;
Flagellae: immotile strain
GRAM: negative coloration
BASE CONDITIONS: 30°, ambient atmosphere
Description of cultures: luxuriant culture, not pigmented, on agar and broth
Aero-anaerobic culture on deep agar
SALINITY (culture medium containing, per liter:
peptone: 10 g; yeast extract: 3 g; glucose: 5 g; pH 7.0–7.2, 30° C., aeration and stirring)

| | | | |
|---|---|---|---|
| NaCl 0% | 3 | 3 | 3 |
| NaCl 2% | 3 | 3 | 3 |
| NaCl 4% | 3 | 3 | 3 |
| NaCl 6% | 3 | 3 | 3 |
| NaCl 8% | 2 | 2 | 2 |
| NaCl 10% | 0 | 1 | 1 |

TEMPERATURE: (Columbia medium, pH 7.0–7.2, aeration)

| | | | |
|---|---|---|---|
| 5° | 0 | 0 | 0 |
| 10° | 0 | 1 | 2 |
| 15° | 1 | 2 | 3 |
| 30° | 3 | 3 | 3 |
| 41° | 3 | 3 | 3 |
| 45° | 3 | 3 | 3 |
| Prototrophic culture | 3 | 3 | 3 |

Culture medium containing, per liter: $KH_2PO_4$: 3.9 g; $K_2HPO_4$: 11.2 g; $(NH_4)_2SO_4$: 2 g; $MgSO_4, 7H_2O$: 200 mg; $FeSO_4, 7H_2O$; 1 ml of a 50 mg/l solution; pH 7.1–7.3

| | | |
|---|---|---|
| CATALASE | 3 | |
| OXIDASE REACTION | 0 | |
| NITRATE REDUCTASE | 3 | 3 |
| TETRATHIONATE REDUCTASE | 0 | 0 |
| THIOSULFATE REDUCTASE | 0 | 0 |

ACID PRODUCTION (culture medium containing, per liter:
bactopeptone: 3 g; NaCl: 5 g; glucose: 10 g; pH 7.2–7.4, in the presence of phenol red)

|  |  |  |  |
|---|---|---|---|
| open tube | 3 | 3 | 3 |
| closed tube | 3 | 3 | 3 |
| VOGES-PROSKAUER TEST | 3 |  |  |

BHI (Brain Heart Infusion) culture medium, pH 7.0–7.2:

|  |  |  |
|---|---|---|
| Gas production (in mm) from glucose | 70 |  |
| ENZYMATIC TESTS (no growing) |  |  |
| UREASE | 0 | 0 |
| INDOLE PRODUCTION | 0 | 0 |
| Gamma-glutamyl transferase | 0 | 0 |
| Phenylalanine deaminase | 0 | 0 |
| Arginine dihydrolase |  | 0 |
| Lysine decarboxylase |  |  |
| Ornithine decarboxylase |  | 0 |
| HYDROLYSIS of o-nitrophenyl-B--D-galactoside | 3 | 3 |
| HYDROLYSIS of p-nitrophenylxyloside | 3 | 3 |
| HYDROLYSIS of ESCULINE | 3 | 3 |
| HYDROLYSIS of TWEEN 80 | 0 | 0 |
| Extracellular DNAse | 0 | 0 |
| Gelatinase (Frazier method) | 0 | 0 |

SYNTHETIC CULTURE MEDIUM: Culture medium containing, per liter: $KH_2PO_4$: 3.9 g; $K_2HPO_4$: 11 g; $(NH_4)_2SO_4$: 2 g;
$MgSO_4, 7H_2O$: 200 mg; $FeSO_4, 7H_2O$: 1 ml of a 50 mg/l solution; aeration and stirring

|  |  |  |  |
|---|---|---|---|
| Citrate | 3 | 3 | 3 |
| Glucose | 3 | 3 | 3 |
| Hydroxy-3-benzoate | 0 | 0 | 0 |
| Hydroxy-5-proline | 0 | 2 | 3 |
| Malonate | 2 | 3 | 3 |

Note: the different columns of results correspond to readings at different times, which could vary from one test to another.
Explanation of symbols:
0: negative reaction or culture
1: weak positive reaction
2: positive reaction
3: intense positive reaction Strain BEC 1000 also has the following nutritional profile. For comparison, the profile for strain ATCC 31646 is also given: substrates which gave a different response are highlighted with an asterisk.

TABLE 1

| Carbon source | Growth/reaction | |
|---|---|---|
|  | BEC 1000 | ATCC 31646 |
| N-acetyl-D-glucosamine | + | + |
| cis-aconitate | + | + |
| trans-aconitate | + | + |
| Adonitol* | + | − |
| D-alanine | + | + |
| L-alanine | + | + |
| 4-aminobutyrate | + | + |
| 5-aminovalerate | + | + |
| L-arabinose | + | + |
| D-arabitol | + | + |
| L-arabitol | − | − |
| D-aspartate | + | + |
| Benzoate | + | + |
| Betaine | − | − |

TABLE 1-continued

| Carbon source | Growth/reaction | |
|---|---|---|
|  | BEC 1000 | ATCC 31646 |
| Caprate | − | − |
| Caprylate | − | − |
| D-cellobiose | + | + |
| Citrate | + | + |
| m-coumarate* | − | + |
| Dulcitol | − | − |
| i-erythritol | − | − |
| Esculine (black color) | + | + |
| Ethanolamine* | + | − |
| D-fructose | + | + |
| L-fucose | + | + |
| Fumarate | + | + |
| D-galactose | + | + |
| D-galacturonate | + | + |
| Gentiobiose | + | + |
| Gentisate | − | − |
| D-gluconate | + | + |
| D-glucosamine | + | + |
| D-glucose | + | + |
| D-glucuronate | + | + |
| L-glutamate | + | + |
| Glutarate | − | − |
| DL-glycerate* | + | − |
| Glycerol | + | + |
| Histamine | − | − |
| L-histidine (pink color) | − | − |
| 3-hydroxybenzoate | − | − |
| 4-hydroxybenzoate | + | + |
| 3-hydroxybutyrate | + | + |
| HQ-β-glucuronide | − | − |
| myo-inositol | + | + |
| Itacoate | − | − |
| 2-ketogluconate | + | + |
| 5-ketogluconate* | − | + |
| 2-ketoglutarate | − | − |
| DL-lactate | + | + |
| Lactose | + | + |
| Lactulose | (+) | (+) |
| D-lyxose | − | − |
| D-malate* | − | + |
| L-malate | + | + |
| Malonate* | + | − |
| Maltitol* | − | + |
| Maltose | + | + |
| Maltotriose | + | + |
| D-mannitol | + | + |
| D-mannose | + | + |
| D-melezitose | − | − |
| D-melibiose | + | + |
| 1-O-methyl-α-galactoside | + | + |
| 1-O-methyl-β-galactoside | + | + |
| 3-O-methyl-D-glucose | − | − |
| 1-O-methyl-α-D-glucoside | (+) | (+) |
| 1-O-methyl-β-D-glucoside | + | + |
| Mucate | + | + |
| Palatinose | + | + |
| Phenylacetate | + | + |
| 3-phenylpropionate | − | − |
| L-proline | + | + |
| Propionate | − | − |
| Protocatechuate | + | + |
| Putrescine | − | − |
| Quinate | + | + |
| D-raffinose | + | + |
| L-rhamnose | + | + |
| D-ribose | + | + |
| D-saccharate | + | + |
| L-serine | + | + |
| D-sorbitol | + | + |
| L-sorbose | + | + |
| Succinate | + | + |
| Sucrose | + | + |
| D-tagatose | − | − |
| D-tartrate | − | − |
| L-tartrate* | − | + |

TABLE 1-continued

| Carbon source | Growth/reaction | |
|---|---|---|
| | BEC 1000 | ATCC 31646 |
| Meso-tartrate | − | − |
| D-trehalose | + | + |
| Tricarballylate* | − | + |
| Trigonelline | − | − |
| Tryptamine | − | − |
| Tryptophan (orange color) | − | − |
| D-turanose | − | − |
| L-tyrosine | − | − |
| Xylitol* | + | − |
| D-xylose | + | − |

Growth was recorded for all substrates except esculine (black colour), hydroxyquinoline-β-glucuronide (black colour), tryptophan (orange/rust colour) and L-histidine (pink/reddish colour), for which only colour development was recorded.

Symbols: +: growth in 1–2 days; (+): growth in 3–4 days; −: no growth in 4 days.

It can be seen that strains BEC 1000 and ATCC 31646 produced 11 responses out of 99 which were different, demonstrating that these strains are distinct from one another.

Strain BEC 1000 was tested for pathogenicity and found to be completely free of virulence for man.

The present invention also concerns mutant strains obtained from strain BEC 1000. Useful mutant strains can be obtained by simple selection of spontaneous mutants isolated from a culture in a fermenter or by subjecting a culture of BEC 1000 to the action of a mutagenic factor, for example energetic radiation (for example UV or X-rays) or to a chemical agent [for example ozone, nitrous acid, NTG (N-methyl-N'-nitro-N-nitrosoguanidine) or EMS (ethanemethane-sulfonate)] in order to kill a large proportion of the microorganisms, then cultivating the microorganisms and selecting those producing more polysaccharides.

Finally, the present invention concerns a process for the production of a polysaccharide with the following chemical structure:

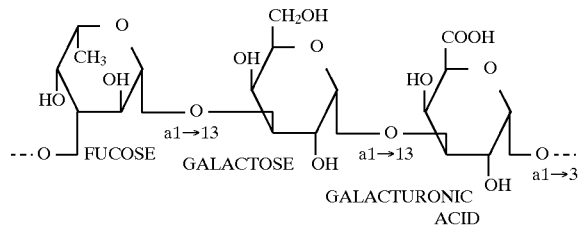

where some of the hydroxyl groups are acetylated, the process comprising (a) growing a microorganism as defined in claim 1 in an aqueous nutrient medium by aerobic fermentation of an assimilatable glucide source, then (b) recovering the polysaccharide from the suspension obtained at the end of step (a).

The polysaccharide is produced by aerobic fermentation, under controlled conditions, of a suitable aqueous nutrient medium inoculated with strain BEC 1000. The medium can be any usual medium containing sources of carbon, nitrogen and mineral salts.

In general, glucides (for example glucose, fructose, maltose, saccharose, mannitol, starch, corn syrup, sorbitol, etc) can be used alone or in combination in the nutrient medium as sources of assimilatable carbon. Sorbitol is a preferred source of carbon. Typically, the quantity of glucides in the medium is between about 2% and 6% by weight of the medium.

Various proteinic materials can be used as the nitrogen source (for example yeast extract, soya flour, protein hydrolysates, corn steep liquor, etc). Typically, the nitrogen source constitutes 0.05% to 0.5% by weight of the medium.

Salts which are normally used in nutrient media can be used as the mineral salts. Non-limiting examples are phosphates, sulphates, chlorides and carbonates of sodium, potassium, ammonium, calcium and magnesium.

Fermentation can be carried out at temperatures of the order of 25° C. to 35° C., preferably 28° C. to 32° C., at a pH of about 6.0 to 7.5, with aeration and stirring, for periods of the order of 2 to 4 days.

Fermentation can be carried out in a conventional fermenter by inoculating the nutrient medium (which has previously been sterilised, for example by heating to a temperature of the order of 120° C. or by sterilising filtration), with a culture of strain BEC 1000.

At the end of the fermentation period, the culture suspension undergoes proteolytic treatment and is then autoclaved, cooled, salted and acidified. The resulting product is treated to separate the polysaccharide, for example by precipitation of the latter using an alcohol (for example methanol, ethanol, propanol or isopropanol) or another polysaccharide non-solvent (such as acetone), then purified by draining and washing the precipitate. If desired, the purification process can be repeated a number of times until a product is obtained which has a purity suitable for the envisaged application.

For use, the purified product can be dissolved in an aqueous solution, in the presence of a preservative, or if desired it can be dried to a powder for storage.

The following non limiting example is provided to illustrate the invention.

EXAMPLE

Production of a polysaccharide containing L-fucose

A polysaccharide containing L-fucose was produced by fermentation in a sorbitol-based culture medium. Production was indicated by a large increase in the apparent viscosity of the medium. At the end portion of the fermentation, this viscosity constituted a limiting element to aeration of the medium. The growth and polysaccharide production kinetics are linked to sorbitol consumption.

PREPARATION OF INOCULUM:

Culture medium:

Neosorb® 70-07 (sorbitol
content: 70% solids;
sold by ROQUETTE FRERES,
Lille, France): 17.90 g/l (i.e., 12.5 g/l of sorbitol)
Biokar® 104003 peptone
(protein hydrolysate, sold by SOLABIA-BIOKAR,
Pantin, France): 4.50 g/l
Yeast extract: 0.05 g/l
$KH_2PO_4$: 1.50 g/l
$K_2HPO_4$: 4.50 g/l
$MgSO_4, 7H_2O$: 0.20 g/l
Pluronic® PE 61000: 0.50 g/l
(antifoaming agent, sold
by BASF, D-6700
Ludwigshafen, Germany)
Dissolution in water.

Culture conditions:
Sterilisation at 121° C. for 30 minutes
Culture temperature: 30° C.
Degree of inoculation: 5% to 10%
Aeration: 1 VVM (volume per volume per minute)
Unregulated pH (pH about 7.00)
Culture period: 24 hours

PRODUCTION MEDIUM

Culture medium:

Neosorb® 70-07: 54.00 g/l (i.e. 38 g/l of sorbitol)
Biokar® 104003 peptone: 4.50 g/l
Yeast extract: 0.05 g/l
$KH_2PO_4$: 1.50 g/l
$K_2HPO_4$: 4.50 g/l
$MgSO_4$, $7H_2O$: 0.20 g/l
Pluronic® PE 61000: 0.50 g/l Dissolution in water.
Culture conditions (Chemap fermenter with a working volume of 350 liters):
Sterilisation at 120° C. for 45 minutes
Culture temperature: 30° C.
Degree of inoculation: about 5%
Stirring: 300 rpm (Rushton type stirrer)
Aeration: 1 VVM
pH regulated to 7.0 by 7 N NaOH
Pressure: 100 to 200 mbars
Culture period: 60 to 65 hours
Average production values:
Viscosity at end of cycle: 40 000 Mpa.s (Brookfield DV-II+ model LV viscosimeter, SP31 rotor, SC4-34/13R chamber, 30° C.)
Concentration of polysaccharide produced in the medium, calculated as L-fucose: 2 g/l (Dische and Shettles method)
Sorbitol consumed: >35 g/l (of sorbitol)
NaOH 20%, weight consumed: 15 liters/$M^3$
Start of pH regulation: 16 to 17 hours after inoculation of fermenter
Final dry extract of fermentation medium: ≈20 g/l
The pH could rise very slightly at the end of the fermentation(pH≈7.2).

POLYSACCHARIDE RECOVERY 500 liters of culture suspension was adjusted to a pH of 8.2 using caustic soda, then underwent proteolytic treatment at 50° C. for 6 hours using 0.5 liter of Alcalase® (subtilisine A from *Bacillus licheniformis* sold by NOVO NORDISK, Denmark). After 6 hours, the pH was brought to 7.0 and the hydrolysate was autoclaved at 120° C., with stirring, for 15 minutes to render the microbic charge inactive, before cooling rapidly to 30° C. and stopping stirring. 20 kg of sodium chloride was then added with stirring and the pH was adjusted to 4.5–5.0. using HCl; stirring was continued for 15 minutes to dissolve the salt completely. At least 85° ethanol was added in a proportion corresponding to 1.1 times the volume of the product, with vigorous stirring. A product precipitated out which was allowed to settle for 4 h to 12 h after stirring was stopped. The supernatant liquor was filtered and returned to a distiller to recover the ethanol for recycling to the precipitation step. The precipitate, which was soaked with a water-alcohol mixture, was dewatered in a Buchner funnel, stirred in a pneumatic deflocculator to eliminate agglomerates, washed with an equal volume of recycled ethanol with stirring, dewatered again in a Buchner funnel, stirred again in the deflocculator, washed with 95° ethanol, stirred and finally dewatered in a Buchner funnel. The dewatered precipitate obtained was then dried for 20 h on plates in an oven at 40° C. The dry product could be stored until required for use. When required for use, the product was dissolved in water with vigorous stirring, for example in a proportion of about 1% by weight, preferably with the addition of a preservative, for example Phenonip® sold by SIPCA (Paris, France).

The pH of the solution was advantageously adjusted to about 7.0.

The product finally obtained was in the form of a viscous, opalescent solution with a very faint odour, with a viscosity of 1 000±200 Mpa.s. This product had remarkable properties, namely:

a relatively high L-fucose content, the anti-allergenic power of which substance has been the subject of a great deal of study;
thickening properties;
good stability over a wide range of pH, temperature and salinity;
a "self-emulsifying" ability;
rheofluidifying behaviour.

which render it eminently suitable for cosmetic formulations such as eye liner products, body milks, products for sensitive skin, baby hygiene products, and others.

It should be noted that other commercially available enzymatic preparations which are equivalent to Alcalase® can be used.

What is claimed is:

1. A biologically pure culture of *Klebsiella pneumoniae* subsp. *pneumoniae*, selected from the group consisting of a strain deposited in the Collection Nationale de Cultures de Microorganismes with registration number I-1507 which can form a polysaccharide containing L-fucose, D-galactose and D-galacturonic acid, and mutants thereof exhibiting increased production of said polysaccharide.

2. A process for the production of a polysaccharide with the following chemical structure:

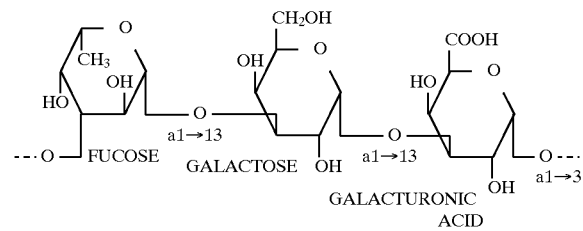

where some of the hydroxyl groups are acetylated, the process comprising (a) growing a microorganism as defined in claim 1 in an aqueous nutrient medium by aerobic fermentation of an assimilatable glucide source, then (b) recovering the polysaccharide.

3. The process according to claim 2 wherein the source of assimilatable glucide is sorbitol.

4. The process according to claim 2 wherein step (b) further comprises hydrolysing the proteins in the culture suspension using an enzymatic route.

5. The process according to claim 2, wherein said fermentation is carried out at a temperature of 25° to 35° C., and a pH of 6.0 to 7.5, with aeration and stirring, for a period of 2 to 4 days.

6. The process according to claim 3 wherein step (b) comprises hydrolysing the proteins in the culture suspension using an enzymatic route.

* * * * *